United States Patent [19]
Fauran et al.

[11] 3,959,270
[45] *May 25, 1976

[54] SUBSTITUTED (5,6,E) INDOLES
[75] Inventors: Claude P. Fauran; Guy M. Raynaud; Michel J. Turin; Claude J. Gouret, all of Paris, France
[73] Assignee: Delalande S.A., Courbevoie, France
[*] Notice: The portion of the term of this patent subsequent to Dec. 3, 1991, has been disclaimed.
[22] Filed: Mar. 21, 1974
[21] Appl. No.: 453,425

Related U.S. Application Data
[63] Continuation-in-part of Ser. No. 260,298, June 6, 1972, Pat. No. 3,852,284.

[30] Foreign Application Priority Data
Mar. 21, 1973  France............................. 73.10202

[52] U.S. Cl............................ 260/244 R; 260/246 R
[51] Int. Cl.². ............. C07D 279/00; C07D 285/00; C07D 295/00
[58] Field of Search........................ 260/244, 246 R

[56] References Cited
OTHER PUBLICATIONS
Grino et al., Chem. Abstracts, Vol. 74, (Item 22645), (1971).

Primary Examiner—Stanley J. Friedman
Assistant Examiner—D. W. Robinson
Attorney, Agent, or Firm—Woodhams, Blanchard and Flynn

[57] ABSTRACT
A compound of the formula

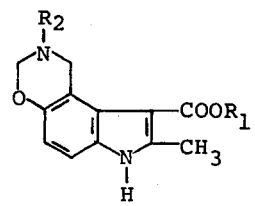

wherein $R_1$ is alkyl having one to 4 carbon atoms, and $R_2$ is (a) alkyl having one to 4 carbon atoms, or (b) alkyl having one to 4 carbon atoms and substituted by (1) dialkylamino the latter alkyl having from one to 3 carbon atoms, (2) pyrrolidino or (3) morpholino, with the proviso that when $R_1$ is ethyl, $R_2$ is not ethyl, propyl, or diethylamino. The compounds are prepared by reacting 2-methyl-3-alkoxycarbonyl-5-hydroxyindole with a primary amine. The compounds possess diuretic, antihypertensive, antiulcerous, antiinflammatory, sedative and analgesic properties.

14 Claims, No Drawings

SUBSTITUTED (5,6,E) INDOLES

CROSS-REFERENCE TO RELATED APPLICATION

This application is a continuation-in-part of our copending application Ser. No. 260,298, filed June 6, 1972 now U.S. Pat. No. 3,852,284.

Our prior patent application Ser. No. 260,298, filed June 6, 1972, relates to novel substituted oxazino (5,6,e) indoles of the formula:

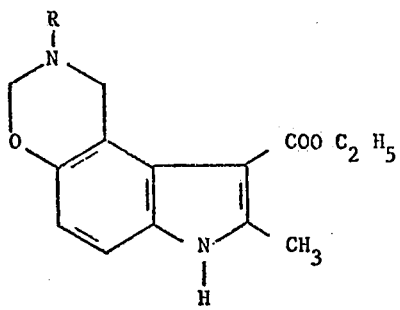

in which R represents:
an alkyl chain containing 2 or 3 carbon atoms optionally substituted by one or more hydroxy or dialkylamino groups, in which the alkyl portion contains up to 4 carbon atoms:
an alkenyl chain containing up to 3 carbon atoms; or a cycloalkyl chain containing up to 6 carbon atoms, the case where the radical R represents an alkyl chain substituted by a dialkylamino group only being illustrated by 3-(diethylaminoethyl)-5-ethoxycarbonyl-6-methyl-2,4-dyhydro-oxazino (5,6,e) indole.

The present application relates to novel compounds, of the same structure as above, and corresponding to the formula:

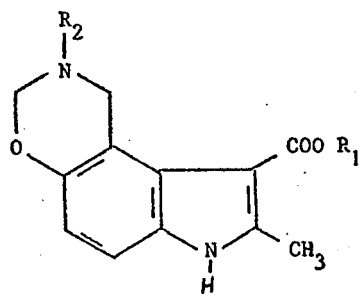

in which:
$R_1$ represents an alkyl radical containing up to four carbon aoms, and
$R_2$ represents an alkyl chain optionally substituted by a dialkylamino group or by a heterocyclic radical selected from pyrrolidino or morpholino,
$R_2$ may not however represent an ethyl, propyl or diethylaminoethyl radical when $R_1$ represents an ethyl radical.

The process according to the invention consists in reacting 2-methyl-3-alkoxycarbonyl-5-hydroxyindole of formula:

with a primary amine of formula:

$R_2 N H_2$       (III)

and an excess of formol, the symbols $R_1$ and $R_2$ having in the formulae (II) and (III), the same significance as in formula (I).

Among the compounds of formula (II) utilizable as starting materials for the process according to the invention, the compounds corresponding to the case where $R_1$ is a methyl radical or a n-propyl radical, are known from the German applicaion published before examination under the No. 1,814,760 and Polish Pat. NO. 59,222, respectively, the material of this latter patent being precized in the extract in "Chemical Abstracts"72 (1970) page 307.

The compounds of formula (II) in which $R_1$ is an isopropyl or n-butyl chain, are themselves novel and are prepared according to Nenitzescu, by the reaction of β-amino crotonates of formula:

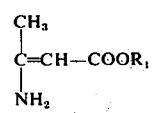

in which $R_1$ represents either the isopropyl or the n-butyl radical, with p-benzoquinone.

By way of example, there is now described the preparation of two of the compounds according to the invention.

EXAMPLE 1

3-i-propyl-5-i-propyloxycarbonyl-6-methyl-2,4-dihydrooxazino (5,6,e) indole

Code No: 72792

1st stage: 2-methyl-3-isopropyloxycarbonyl-5-hydroxy indole.

Code No.: 72777

0.2 mol of β-amino isopropyl crotonate in solution in 200 c.c. of dichlorethane are added, over a period of 6 hours, to a solution, under reflux, of 0.25 mol of p-benzoquinone in 100 c.c. of dichlorethane. The water formed is progressively eliminated. After a supplementary reflux for 1½ hours, the mixture is cooled and the 2-methyl-5-hydroxy-3-indole isopropyl carboxylate formed is filtered off.

| Melting point | = | 234°C |
| Yield | = | 30% |
| Empirical formula | = | $C_{13}H_{15}NO_3$ |

Elementary analysis:

|  | C | H | N |
|---|---|---|---|
| Calculated % | 66.93 | 6.48 | 5.01 |
| Found % | 67.13 | 6.44 | 6.21 |

2nd stage: 3-i-propyl-5-i-propyloxycarbonyl-6-methyl-2,4-dihydro oxazino (5,6,e) indole.

Code No: 72 792

50 ml of dioxane and 18 ml of a solution of 40% formaldehyde are introduced into a 1 liter balloon-flask. 9g of isopropylamine are then added at a temperature below 10°C, followed by 23g of 2-methyl-3-i-propyloxycarbonyl-5-hydroxyindole. The mixture is then maintained under reflux for 5 hours and is then cooled. The precipitate formed is dried and then recrystallized from absolute alcohol.

| Melting point | = | 165°C |
| --- | --- | --- |
| Yield | = | 44% |
| Empirical formula | = | $C_{18}H_{24}N_2O_3$ |

Elementary analysis:

|  | C | H | N |
| --- | --- | --- | --- |
| Calculated % | 68.33 | 7.65 | 8.86 |
| Found % | 68.46 | 7.59 | 8.76 |

EXAMPLE 2

3-i-propyl-5-n-butoxycarbonyl-6-methyl-2,4-dihydro oxazino (5,6,e) indole.

Code No. 72 813

1st stage: 2-methyl-3-butoxycarbonyl-5-hydroxyindole
Code No: 72 799

0.2 mol of β-amino butyl crotonate in solution in 150 c.c. of dichlorethane is added, over a period of 15 hours, to a solution under reflux of 0.25 mol of p-benzoquinone in 150 c.c. of dichlorethane. The water formed is progressively eliminated. After a supplementary reflux for 1 hour, the mixture is cooled and the 2-methyl-5-hydroxy-3-indole butyl carboxylate formed is filtered off.

| Melting point | = | 183°C |
| --- | --- | --- |
| Yield | = | 23% |
| Empirical formula | = | $C_{14}H_{17}NO_3$ |

Elementary analysis:

|  | C | H | N |
| --- | --- | --- | --- |
| Calculated % | 67.99 | 6.93 | 5.66 |
| Found % | 68.80 | 6.87 | 5.82 |

2nd stage: 3-i-propyl-5-n-butoxycarbonyl-6-methyl-2,4-dihydro oxazino (5,6,e) indole.

This stage is analogous to the second stage of Example 1. The product obtained possesses the following characteristics:

| Melting point | = | 138°C |
| --- | --- | --- |
| Yield | = | 37% |

Elementary analysis:

|  | C | H | N |
| --- | --- | --- | --- |
| Calculated % | 69.06 | 7.93 | 8.48 |
| Found % | 68.98 | 8.12 | 8.37 |

The compounds listed in the following Table I have been prepared according to the same method of preparation.

TABLE I

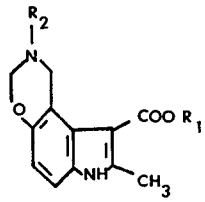

| Code No. | $R_1$ | $R_2$ | Empirical formula | Molecular weight | Melting point (°C) | Yield (%) | Calculated % C | Calculated % H | Calculated % N | Found % C | Found % H | Found % N |
| --- | --- | --- | --- | --- | --- | --- | --- | --- | --- | --- | --- | --- |
| 72 572 | $C_2H_5$ | —$CH_3$ | $C_{15}H_{18}N_2O_3$ | 274.31 | 170 | 51 | 65.67 | 6.61 | 10.21 | 65.73 | 6.50 | 10.23 |
| 72 549 | $C_2H_5$ | —$C_4H_9$ (n) | $C_{18}H_{24}N_2O_3$ | 316.39 | 144 | 45 | 68.33 | 7.65 | 8.85 | 68.44 | 7.66 | 8.90 |
| 72 550 | $C_2H_5$ | —$C_4H_9$ (t) | $C_{18}H_{24}N_2O_3$ | 316.39 | 175 | 61 | 68.33 | 7.65 | 8.85 | 68.31 | 7.66 | 9.01 |
| 72 393 | $C_2H_5$ | —$(CH_2)_2N(CH_3)_2$ | $C_{18}H_{25}N_3O_3$ | 331.40 | 170 | 45 | 65.23 | 7.60 | 12.68 | 65.08 | 7.59 | 12.76 |
| 72 439 | $C_2H_5$ | —$(CH_2)_3N(C_2H_5)_2$ | $C_{21}H_{31}N_3O_3$ | 373.48 | 106 | 16 | 67.53 | 8.37 | 11.25 | 67.62 | 8.31 | 11.06 |
| 72 394 | $C_2H_5$ | —$(CH_2)_2$—N◯ (piperidine) | $C_{20}H_{27}N_3O_3$ | 357.44 | 194 | 64 | 67.20 | 7.61 | 11.76 | 67.00 | 7.50 | 11.81 |
| 72 365 | $C_2H_5$ | —$(CH_2)_2$—N◯O (morpholine) | $C_{20}H_{27}N_3O_4$ | 373.44 | 189 | 62 | 64.32 | 7.29 | 11.25 | 64.18 | 7.43 | 11.06 |
| 72 564 | $CH_3$ | —$C_3H_7$ (i) | $C_{16}H_{20}N_2O_3$ | 288.34 | 212 | 85 | 66.64 | 6.99 | 9.72 | 66.46 | 7.19 | 9.77 |
| 72 723 | $CH_3$ | —$(CH_2)_2N(C_2H_5)_2$ | $C_{19}H_{27}N_3O_3$ | 345.43 | 108 | 48 | 66.06 | 7.88 | 12.17 | 66.07 | 8.04 | 11.97 |
| 72 762 | $CH_3$ | —$(CH_2)_2$N◯O | $C_{19}H_{25}N_3O_4$ | 359.41 | 192 | 40 | 63.49 | 7.01 | 11.67 | 63.69 | 6.93 | 11.57 |
| 72 780 | $C_3H_7$ (n) | —$C_3H_7$ (i) | $C_{18}H_{24}N_2O_3$ | 316.39 | 160 | 53 | 68.33 | 7.65 | 8.85 | 68.30 | 7.87 | 8.98 |
| 72 786 | $C_3H_7$ (n) | —$(CH_2)_2N(C_2H_5)_2$ | $C_{21}H_{31}N_3O_3$ | 373.48 | 116 | 48 | 67.53 | 8.37 | 11.25 | 67.46 | 8.34 | 11.37 |
| 72 730 | $C_3H_7$ (n) | —$(CH_2)_2$N◯O | $C_{21}H_{29}N_3O_4$ | 387.47 | 152 | 28 | 65.09 | 7.54 | 10.85 | 64.94 | 7.65 | 11.01 |
| 72 800 | $C_3H_7$ (i) | —$(CH_2)_2N(C_2H_5)_2$ | $C_{21}H_{31}N_3O_3$ | 373.48 | 152 | 47 | 67.53 | 8.37 | 11.25 | 67.66 | 8.17 | 11.28 |
| 72 807 | $C_3H_7$ (i) | —$(CH_2)_2$N◯O | $C_{21}H_{29}N_3O_4$ | 387.47 | 197 | 60 | 65.09 | 7.54 | 10.85 | 65.29 | 7.65 | 10.82 |
| 72 824 | $C_4H_9$ (n) | —$(CH_2)_2$N◯O | $C_{22}H_{31}N_3O_4$ | 401.49 | 139 | 56 | 65.81 | 7.78 | 10.47 | 65.98 | 7.79 | 10.67 |

The compounds of formula (I) have been tested on animals in the laboratory and have been shown to possess diuretic, antihypertensive, antiulcerous, antiinflammatory, sedative and analgesic properties.

1. Diuretic properties

The compounds of formula (I) administered by oral means to the mouse, simultaneously with a volume of 1 ml. of an isotonic solution of sodium chloride per 25g of the corporeal weight of the mouse and to the rat simultaneously with a volume of 2.5ml of solution per 100 g of the corporeal weight of the rat, are capable of provoking an augmentation of the volume of urine emitted by reference to control animals, the volume being measured for three hours following administration.

By way of example, the following Table II lists the results obtained by the administration of different compounds of formula (I).

TABLE II

| Code No. of compound tested | Animal | Dose doubling the volume of urinary emission (mg/kg/p.o.) |
|---|---|---|
| 72 550 | mouse | 14 |
| 72 572 | mouse | 40 |
| 72 393 | mouse | 11 |
| 72 365 | mouse | 4.3 |
|  | rat | 0.5 |
| 72 394 | mouse | 20 |
| 72 564 | mouse | 25 |
| 72 723 | mouse | 14 |
| 72 730 | mouse | 8 |
| 72 762 | mouse | 9 |
| 72 780 | mouse | 35 |
| 72 800 | mouse | 20 |
| 72 807 | mouse | 12 |
| 72 824 | mouse | 16 |

Also, the compounds of formula (I) and, in particular the compounds of Code Nos. 72 550, 72 393, 72 365, 72 394, 72,564, 72 723, 72 730 72 762, 72 800, 72 807 and 72 824 possess a superior diuretic power than the compounds of the parent application since this latter application mentions, by way of example, that the compound of code No. 71 134, administered in a dose of 20mg/kg/p.o. only augments the diureses by 65%.

This Table shows, as well, that certain compounds according to the present addition, more notably, the compounds of Code Nos. 72 393, 72 730, 72 762, and 72 365 are more active than the furosamide corresponding to the formula:

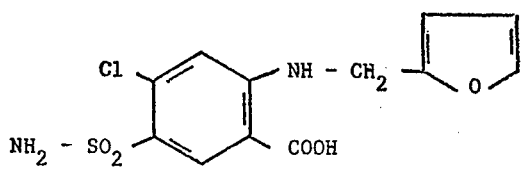

since it is necessary to administer this latter compound in a dose of 10 mg/kg/p.o. to the rat, in order to observe an augmentation of the urinary elimination of 90% and in a dose of 12.5 mg/kg/p.o. to the mouse in order to double the diuresis.

2. Antihypertensive properties

The compounds of formula (I), administered by oral means to a rat suffering from high blood pressure, are capable of lowering the systolic arterial pressure.

By way of example, the administration of 50 mg/kg/p.o. of the compound of Code Nos 72 365 brought down to the normal value the systolic arterial pressure of rats suffering from high blood pressure in 43% of the animals treated.

3. Antiulcerous properties

The compounds of formula (I), administered by intraduodenal means, reduce the extent of ulceration provoked in a rat by tying of the pylorus (Shay ulcers).

Thus, the administration of 50 mg/kg/i.d. of the compound of Code No. 72 439, produces a reduction of the Shay ulcers by 35%.

4. Antiinflammatory properties

These properties are shown by a diminution of the local oedema caused by the sub-plantar injection of a phlogogenic agent, such as carraghenin, in the rat, following the oral administration of the compounds of formula (I).

It is to be noted, by way of example, that the administration of 100 mg/kg/p.o. of the compounds of Code Nos. 72786 and 72 800 permits a reduction of the oedema caused by the sub-plantar injection of carraghenin, by 55% and 45% respectively.

5. Sedative properties

The compounds of formula (I), administered by oral means to the mouse reduce the number of explorations in the evasion enclosure.

By way of example, the administration of 100 mg/kg/p.o. of the compound of Code No. 72 800 produces a reduction of 30% in the number of explorations in the evasion enclosure.

6. Analgesic properties

The compounds of formula (I) administered by oral means to the mouse, are capable of reducing the number of painful stretchings caused by the intraperitoneal injection of acetic acid.

Thus, the administration of 100 mg/kg/p.o. of the compounds of Code Nos. 72 723 and 72 786, produces a reduction in the number of painful stretchings of 43% and 40% respectively.

As a result of a comparison between the pharmacologically active doses cited previously and the lethal doses listed in the following Table III the difference between these doses is sufficiently great to permit the utilization of the compounds of formula (I) in therapeutics.

TABLE III

| Code No. of compound tested | DL 50 (mg/kg/p.o.) |
|---|---|
| 72 550 | 435 |
| 72 393 | 600 |
| 72 365 | 540 |
| 72 394 | 720 |
| 72 439 | 900 |
| 72 564 | 1650 |
| 72 723 | 1000 |
| 72 730 | 800 |
| 72 762 | 955 |
| 72 786 | 1250 |
| 72 800 | 1200 |
| 72 807 | 920 |
| 72 824 | 720 |

The compounds of formula (I) are useful in the treatment of oedemas, hypertension, gastro-duodenal ulcers, anxiety, nervousness, inflammatory pains and diverse originating pains.

They may be administered by oral means in the form of tablets, gelules and dragees containing 12.5 to 200 mg of active ingredient (1 to 4 times per day), by parenteral means in the form of injectable ampoules containing 10 to 100 mg of active ingredient (1 or 2 per day) and by rectal means in the form of suppositories containing 20 to 150 mg of active ingredient (1 or 2 times per day).

Accordingly, the present invention also relates to a therapeutic composition comprising a compound of the general formula (I) together with a therapeutically acceptable carrier.

What we claim is:

1. A compound having the formula

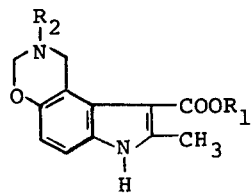

in which $R_1$ is alkyl having 1 to 4 carbon atoms, and $R_2$ is alkyl having 1 to 4 carbon atoms or alkyl having 1 to 4 carbon atoms substituted by dialkylamino, pyrrolidino or morpholino, with the proviso that when $R_1$ is ethyl, $R_2$ is not ethyl, propyl, or ethyl and propyl substituted by dialkylamino.

2. A compound as claimed in claim 1 in which $R_2$ is morpholinoethyl.

3. A compound as claimed in claim 1 in which $R_1$ is ethyl and $R_2$ is pyrrolidinoethyl.

4. A compound as claimed in claim 1 in which $R_1$ is ethyl and $R_2$ is t-butyl.

5. A compound as claimed in claim 1 in which $R_1$ is methyl and $R_2$ is i-propyl.

6. A compound as claimed in claim 1 in which $R_1$ is methyl and $R_2$ is diethylaminoethyl.

7. A compound as claimed in claim 1 in which $R_1$ is n-propyl and $R_2$ is diethylaminoethyl.

8. A compound as claimed in claim 1 in which $R_1$ is i-propyl and $R_2$ is diethylaminoethyl.

9. A compound as claimed in claim 1 in which $R_1$ is ethyl and $R_2$ is methyl.

10. A compound as claimed in claim 1 in which $R_1$ is ethyl and $R_2$ is morpholinoethyl.

11. A compound as claimed in claim 1 in which $R_1$ is methyl and $R_2$ is morpholinoethyl.

12. A compound as claimed in claim 1 in which $R_1$ is n-propyl and $R_2$ is morpholinoethyl.

13. A compound as claimed in claim 1 in which $R_1$ is i-propyl and $R_2$ is morpholinoethyl.

14. A compound as claimed in claim 1 in which $R_1$ is n-butyl and $R_2$ is morpholinoethyl.

* * * * *